US006347241B2

(12) United States Patent
Burbank et al.

(10) Patent No.: US 6,347,241 B2
(45) Date of Patent: *Feb. 12, 2002

(54) ULTRASONIC AND X-RAY DETECTABLE BIOPSY SITE MARKER AND APPARATUS FOR APPLYING IT

(75) Inventors: Fred H. Burbank, San Juan Capistrano; Paul Lubock, Laguna Niguel; Michael L. Jones, Capistrano Beach; Nancy Forcier, Laguna Niguel, all of CA (US)

(73) Assignee: SenoRx, Inc., Aliso Viejo, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/343,975

(22) Filed: Jun. 30, 1999

Related U.S. Application Data

(63) Continuation-in-part of application No. 09/241,936, filed on Feb. 2, 1999, now Pat. No. 6,161,034.

(51) Int. Cl.⁷ .............................................. A61B 19/00
(52) U.S. Cl. ........................ 600/431; 600/130; 378/62
(58) Field of Search ................................ 600/431, 432, 600/426; 606/130; 378/62, 37, 162

(56) References Cited

U.S. PATENT DOCUMENTS

| 2,192,270 A | | 3/1940 | McGowan |
| 3,341,417 A | * | 9/1967 | Sinaiko ........................ 606/130 |
| 3,823,212 A | | 7/1974 | Chvapil |
| 4,172,449 A | * | 10/1979 | LeRoy et al. ................ 600/431 |
| 4,197,846 A | | 4/1980 | Bucalo |
| 4,276,885 A | * | 7/1981 | Tickner et al. .............. 424/9.52 |
| 4,294,241 A | | 10/1981 | Miyata |
| 4,813,062 A | * | 3/1989 | Gilpatrick ................... 378/162 |
| 4,847,049 A | | 7/1989 | Yamamoto |
| 4,863,470 A | * | 9/1989 | Carter ............................ 623/8 |

(List continued on next page.)

FOREIGN PATENT DOCUMENTS

| EP | 0255 123 | 2/1988 |
| EP | 0292 936 | 11/1988 |
| WO | 98/06346 | 2/1998 |
| WO | 99 30764 | 6/1999 |

OTHER PUBLICATIONS

Fucci, V., et al, "Large Bowel Transit Times Using Radioopaque Markers in Normal Cats", J. of Am. Animal Hospital Assn., Nov.–Dec. 1995 31 (6) 473–7.*

Schindlbeck, N.E., et al., "Measurement of Colon Transit Time", J. of Gastroenterology, No. 28, pp. 399–404, 1990.*

*Primary Examiner*—John A. Jeffery
(74) *Attorney, Agent, or Firm*—Coudert Brothers LLP

(57) ABSTRACT

A biopsy site marker comprises small bodies or pellets of gelatin which enclose substantially in their interior a radio (X-ray) opaque object. The gelatin pellets are deposited into the biopsy site, typically a cylindrical opening in the tissue created by the recent use of a vacuum assisted large core biopsy device, by an applicator device that includes an elongated cylindrical body that forms a flexible tube and a piston slidable in the tube. One end of the tube is placed into the biopsy site. Typically, several gelatin pellets, only some of which typically do, but all of which may contain the radio opaque object, are deposited sequentially into the site through the tube. The radio opaque objects contained in the gelatin bodies are of a non-biological configuration and readily identifiable as man-made object, so that in observation by typical mammography equipment they do not assume the shape of a line, whereby they are readily distinguishable from granules and lines of calcification.

23 Claims, 3 Drawing Sheets

U.S. PATENT DOCUMENTS

| | | |
|---|---|---|
| 4,909,250 A | 3/1990 | Smith |
| 5,147,307 A | 9/1992 | Gluck |
| 5,368,030 A * | 11/1994 | Zinreich et al. ............ 324/309 |
| 5,395,319 A | 3/1995 | Hirsh et al. |
| 5,433,204 A | 7/1995 | Olson |
| 5,853,366 A * | 12/1998 | Dowlatshahi ................ 600/434 |
| 6,056,700 A * | 5/2000 | Burney et al. .............. 606/167 |
| 6,161,034 A * | 12/2000 | Burbank et al. ............. 600/431 |
| 6,234,177 B1 * | 5/2001 | Barsch ....................... 128/897 |

* cited by examiner

US 6,347,241 B2

ULTRASONIC AND X-RAY DETECTABLE BIOPSY SITE MARKER AND APPARATUS FOR APPLYING IT

RELATED APPLICATIONS

This application is a continuation-in-part application to application Ser. No. 09/241,936, filed on Feb. 2, 1999, now U.S. Pat. No. 6,161,034.

BACKGROUND OF THE INVENTION

1. Field of the Invention

The present invention is in the field of markers to be employed at biopsy sites to permanently mark the site, and to methods and apparatus for applying the permanent marker. More particularly, the present invention relates to a marker that is optimally adapted for marking biopsy sites in human breast tissue with permanently placed markers that are detectable by X-ray.

2. Brief Description of the Background Art

In modern medical practice small tissue samples, known as biopsy specimens, are often removed from tumors, lesions, organs, muscles and other tissues of the body. The removal of tissue samples may be accomplished by open surgical technique, or through the use of a specialized biopsy instruments such as a biopsy needle. A well known state-of-the-art instrument that is often used in connection with the practice of the present invention is known as the "vacuum assisted large core biopsy device".

After a tissue sample has been removed, it is typically subjected to diagnostic tests or examinations to determine cytology, histology, presence or absence of chemical substances that act as indicators for disease status, or the presence of bacteria or other microbes. The above mentioned and other diagnostic tests and examinations per se are well known in the art and need not be described here. It is sufficient to note that the information obtained from these diagnostic tests and/or examinations is often of vital importance for the well-being of the patient and is used to make or confirm diagnoses and often to formulate treatment plans for the patient. As is known, obtaining a tissue sample by biopsy and the subsequent examination are frequently, almost invariably, employed in the diagnosis of cancers and other malignant tumors, or to confirm that a suspected lesion or tumor is not malignant, and are frequently used to devise a plan for the appropriate surgical procedure or other course of treatment.

Examination of tissue samples taken by biopsy, often by the above-mentioned "vacuum assisted large core biopsy sampler" is of particular significance in the diagnosis and treatment of breast cancer which is the most common cancer suffered by women in the U.S.A and elsewhere in the industrially developed world. Proper diagnostic procedures, frequent examination by well known techniques such as "mammography" and prompt subsequent surgical treatment have, however, significantly reduced the mortality rate caused by this form of cancer. For this reason, in the ensuing discussion of the pertinent background art and in the ensuing description the invention will be described as used for marking biopsy sites in human and other mammalian breast, although the invention is suitable for marking biopsy sites in other parts of the human and other mammalian body as well.

Thus, as is known, when an abnormal mass in the breast is found by physical examination or mammography a biopsy procedure follows almost invariably. The nature of the biopsy procedure depends on several factors. Generally speaking, if a solid mass or lesion in the breast is large enough to be palpable (i.e., felt by probing with the fingertips) then a tissue specimen can be removed from the mass by a variety of techniques, including but not limited to open surgical biopsy or a technique known as Fine Needle Aspiration Biopsy (FNAB). In open surgical biopsy, an incision is made and a quantity of tissue is removed from the mass for subsequent histopathological examination. In the FNAB procedure, a small sample of cells is aspirated from the mass through a needle and the aspirated cells are then subjected to cytological examination.

If a solid mass of the breast is small and non-palpable (e.g., the type typically discovered through mammography), a relatively new biopsy procedure known as "stereotactic needle biopsy" may be used. In performing a stereotactic needle biopsy of a breast, the patient lies on a special biopsy table with her breast compressed between the plates of a mammography apparatus and two separate digital x-rays are taken from two slightly different points of view. A computer calculates the exact position of the lesion with X and Y coordinates as well as depth of the lesion within the breast. Thereafter, a mechanical stereotactic apparatus is programed with the coordinates and depth information calculated by the computer, and such apparatus is used to precisely advance the biopsy needle into the small lesion. Usually at least five separate biopsy specimens are obtained from locations around the small lesion as well as one from the center of the lesion.

After the biopsy sample is taken, it may take several days or even a week before the results of the examination of the sample are obtained, and still longer before an appropriate treatment decision is reached. If the decision involves surgery it is clearly important for the surgeon to find the location in the breast from where the tumor tissue has been taken in the biopsy procedure, so that the entire tumor and possibly surrounding healthy tissue can be removed. For example, the particular treatment plan for a given patient may require the surgeon to remove the tumor tissue and 1 centimeter of the tissue surrounding the tumor. A co-pending application for United States Letters Patent by the same inventors discloses markers which are particularly well adapted for marking biopsy sites in the human breast, and which markers remain detectable by X-ray, ultrasound or some other detection technique only for a given time period (i.e. for 6 months) and slowly disappear thereafter, for example by absorption into the body. The purpose of such markers is to facilitate the surgical procedure that is performed while the marker is still detectable. The disappearance of the marker after a longer period of time may be advantageous to avoid obscuring or interfering with follow-up studies or further mammography or other imaging studies.

In connection with the background art the following specific printed art is mentioned. U.S. Pat. Nos. 2,192,270 and 5,147,307 describe visually discernible markers that are applied externally to the patient's skin. Radiographically (X-ray) detectable tissue markers (e.g., clips or staples) that are attached to tissue adjacent to the site from which the biopsy specimen has been removed, are described in International Patent Publication No. WO 98/06346. Radiographically visible markers (e.g. marker wires) that may be introduced into the biopsy site and are inserted through the biopsy needle after a tissue sample is removed and which are thereafter allowed to remain protruding from the patient's body, are also described in WO 98/06346. However, due to the consistency of breast tissue and the fact that these biopsy site markers are typically introduced while the breast is still compressed between the mammography plates, these biopsy markers of the prior art may become attached to adjacent bands of connective tissue that do not remain at the specific location of the biopsy after the breast has been decompressed and removed from the mammography apparatus, and may suffer from additional disadvantages as well.

Thus, there is still a need in the art for of biopsy site markers that are deliverable into the cavity created by removal of the biopsy specimen and not into tissue that is located outside of that biopsy cavity, and which will not migrate from the biopsy cavity even when the breast tissue is moved, manipulated or decompressed. Moreover, such desired markers should remain detectable at the biopsy site i. e. within the biopsy cavity for an indefinite time period, and still should not interfere with imaging of the biopsy site and adjacent tissues at a later point of time, and most importantly should be readily distinguishable in the various imaging procedures from lines of calcifications which frequently are signs for a developing malignancy. The present invention provides such permanent biopsy site markers as well as apparatus and method for delivering such markers into the biopsy cavity.

SUMMARY OF THE INVENTION

It is an object of the present invention to provide a biopsy site marker that is deliverable into the cavity created by removal of the biopsy specimen.

It is another object of the present invention to provide a biopsy site marker that does not migrate from the biopsy cavity even when the surrounding tissue is moved, manipulated or decompressed.

It is still another object of the present invention to provide a biopsy site marker that meets the foregoing requirements and that remains detectable at the biopsy site for an indefinite period of time.

It is yet another object of the present invention to provide a biopsy site marker that meets the foregoing requirements and that is readily distinguishable by X-ray from granules or lines of calcifications which frequently are signs for a developing malignancy.

It is a further object of the present invention to provide an apparatus and method for placing into the biopsy cavity a biopsy site marker that meets the foregoing requirements.

These and other objects and advantages are attained by a biopsy site marker that comprises small bodies or pellets of gelatin which enclose substantially in their interior a radio (X-ray) opaque object. The gelatin pellets are deposited into the biopsy site, typically a cylindrical opening in the tissue created by the recent use of a vacuum assisted large core biopsy device, by injection from an applicator through a tube that is placed into the biopsy site. Typically, several gelatin pellets, only some of which typically do, but all of which may contain the radio opaque object, are deposited sequentially from the applicator into the site through the tube. The radio opaque objects contained in the gelatin bodies have a non-biological shape or configuration to be identifiable as a man-made object such that in observation by typical mammography equipment, that is when viewed from at least two different viewing angles, they do not assume the shape of a line, whereby they are readily distinguishable from granules or lines of calcification.

The features of the present invention can be best understood together with further objects and advantages by reference to the following description, taken in connection with the accompanying drawings, wherein like numerals indicate like parts.

DESCRIPTION OF THE PREFERRED EMBODIMENTS

The following specification taken in conjunction with the drawings sets forth the preferred embodiments of the present invention. The embodiments of the invention disclosed herein are the best modes contemplated by the inventors for carrying out their invention in a commercial environment, although it should be understood that various modifications can be accomplished within the parameters of the present invention.

Figure 1:
FIG. 1 is a perspective view of a preferred embodiment of the biopsy site marker of the present invention.
Figure 2:
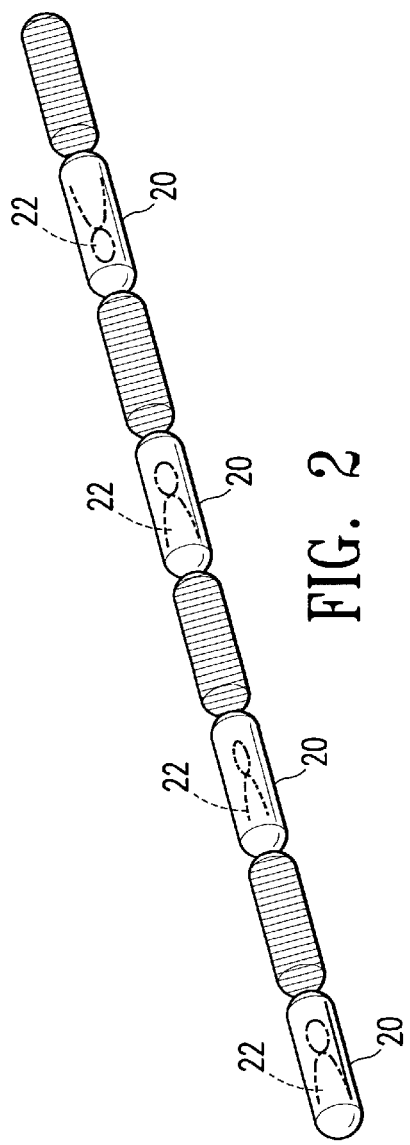
FIG. 2 is a perspective view of a plurality of biopsy site markers in accordance with the first embodiment of the present invention.

Referring now to the drawing figures and particularly to FIGS. 1 and 2, a body 20 of gelatin or reconstituted collagen in the shape of a pellet that includes or incorporates a radio-opaque marker 22 of a definite shape is disclosed. The gelatin or reconstituted collagen body 20 can be of virtually any shape or configuration, however the herein shown shape of a cylinder or pellet is preferred. The gelatin body of pellet 20 is of such size that several of the pellets can be deposited in a biopsy site, such as a typical biopsy site obtained by using the vacuum assisted large core biopsy device that is frequently used in current medical practice. The gelatin body or pellet 20 is stored and is applied, that is deposited in the biopsy site, in a dehydrated form through an applicator device that forms another aspect of this invention. However, when the gelatin body or pellet 20 of the invention is not deposited through the applicator device, it does not necessarily need to be stored and applied in a dehydrated form. Nevertheless, storing the gelatin pellets 20 in dehydrated form increases their useful shelf-life and renders it easier to keep them sterile.

After having been deposited at the biopsy site the gelatin marker 20 slowly absorbs moisture from the surrounding tissue and becomes hydrated. In the dehydrated form, shown in the appended drawing figures, the gelatin body or pellet 20 is approximately 1 to 3 mm in diameter and is approximately 5 to 10 mm long. The presently preferred embodiment of the gelatin pellet 20 is approximately 2 mm in diameter and is approximately 8 mm long. After the pellet 20 has reached hydration equilibrium with the surrounding tissue it becomes approximately 3 to 5 mm in diameter and approximately 10 to 15 mm long. After hydration the presently preferred embodiment of the pellet 20 is approximately 4 mm in diameter and approximately 10 mm long.

The gelatin or reconstituted collagen material itself is observed under ultrasound examination as a white spot because of the air pockets usually entrapped in its matrix. In mammography the gelatin is observed as dark spots in normal breast, because of the presence of the air pockets. In a fatty breast viewed by mammography the gelatin marker is observed as a lighter area containing dark spots, due to the water in the hydrated gelatin absorbing more energy than the surrounding matrix and the air pockets within the matrix. A pellet 20 or plurality of pellets 20 due to their bulk may also be palpable and locatable by tactile means within the breast tissue or other tissue. The gelatin or reconstituted collagen marker itself can be made even more radio-opaque by ion-impregnation and chelation techniques which are described in detail in the aforesaid co-pending application Ser. No. 09/241,936 filed on Feb. 2, 1999 by the same inventors in connection with the description of biopsy markers of that application, and the description of this method of rendering the gelatin markers radio-opaque is also provided here below. The disclosure of co-pending application Ser. No. 09/241,936 is incorporated herein by reference in its entirety. The gelatin or reconstituted collagen material can also be made more radio-translucent by entrapping (mixing) a substantial amount of air in the gelatin. Moreover, a visually detectable substance, such as carbon particles, or a suitable dye (e.g. methylene blue or indigo) may also be added to the gelatin to make the marker visible by a surgeon during dissection of the surrounding breast tissue.

The gelatin or reconstituted collagen per se does not serve as a permanent marker of the biopsy site because it is eventually reabsorbed by the body, although the dye or even ionic material that made the gelatin visible or radio-opaque, respectively, may remain at the site for longer time period than the palpable gelatin pellet, and may remain there indefinitely. Factors which influence how long the gelatin or reconstituted collagen pellet remains at the site, and various means to adjust this time period are described in the aforementioned co-pending application Ser. No. 09/241,936.

It is a novel and important aspect of the present invention to incorporate into the gelatin or reconstituted collagen body or pellet 20 the radio-opaque marker 22. The radio-opaque or X-ray detectable marker 22 that is incorporated or enclosed in the gelatin pellet 20 must have the following properties. First, by its very nature it must be detectable by X-ray, including the type of radiography used in the practice of mammography. It must be comprised of a material or composition that is not absorbed by the body and stays for indefinite time at the biopsy site, retains its shape and remains X-ray detectable at the biopsy site also for an indefinite time. The material or composition of the radio-opaque marker 22 must, of course, be biocompatible at the site where it is deposited. Another important requirement is that the biocompatible marker must have an identifiable specific non-biological shape or form. The purpose of specific form for the marker is to render the marker distinguishable under X-ray or in a mamographic examination from naturally formed calcification granules or a line of such granules, which are also X-ray opaque. As is known, a line of calcification which normally forms along ducts is considered a sign of developing malignancy. Thus, the marker 22 should be of such specific configuration that when it is viewed sterically, as during a mammography examination, it should be distinguishable from an X-ray opaque line. Numerous specific shapes or configurations satisfy the foregoing requirements, however amorphous X-ray opaque material that would be uniformly (or substantially uniformly) distributed in the gelatin pellet 20 is unlikely to satisfy these requirements.

Materials or compositions which are suitable for the marker 22 include metal, such as stainless steel, tantalum, titanium, gold, platinum, palladium, various alloys that are normally used in bioprosthesis and ceramics and metal oxides that can be compressed into specific shapes or configurations. Among these the use of biocompatible metals is presently preferred, and the herein described preferred embodiment of the marker 22 is made of stainless steel. Generally speaking the marker 22 is approximately 0.010 to 0.060 inches wide, approximately 0.030 to 0.200" long and approximately 0.002 to 0.020" thick. The presently preferred permanent marker 22 shown in the drawing figures has the configuration or shape approximating an upside down turned Greek letter gamma ($\gamma$), is approximately 0.10" long and approximately 0.040" wide. The upside-down Greek letter gamma ($\gamma$) shape is believed to be unique, has some resemblance to the popular breast cancer awareness ribbon and is readily distinguishable under X-ray and mammography as a "man-made" marker object from any naturally formed X-ray opaque body. Various manufacturing techniques which per se are well known in the art, can be utilized to manufacture the X-ray opaque permanent marker 22. Thus, the marker 22 can be formed from wire, or can be electrochemically etched or laser cut from metal plates. The presently preferred embodiment of the gamma ($\gamma$) shaped marker 22 is formed by electrochemical etching from stainless steel plates.

FIGS. 1, 2 and the other drawing figures, as applicable, show only one marker in the gelatin pellet 20, although more than marker may be incorporated in the pellet 20. FIG. 1 discloses a cylindrically shaped gelatin pellet 20 that in accordance with the present invention includes the gamma ($\gamma$) shaped stainless marker 22, and as an optional feature also includes a dye or other coloring material (e.g. indigo) that also stays substantially permanently at the biopsy site and is visible by a surgeon when the breast tissue is dissected, as in an operation where tumor tissue is removed (lumpectomy). Gelatin bodies or pellets 20 all of which include one or more permanent radio opaque markers 22 in accordance with the present invention may be deposited at a biopsy site. Alternatively, a series of gelatin bodies or pellets 20 where only some but not all include a permanent X-ray opaque marker 22 of unique non-biological shape, may be deposited at the biopsy site. Preferably, a series of pellets 20 are deposited where each second, each third, or each fourth etc., pellet includes the marker 22. FIG. 2 discloses an example of a series or sequence of pellets 20 where each second pellet 20 includes the metal marker 22 and where each pellet 20 that does not include the metal marker 22 includes carbon black or dye that is visible to the surgeon during operation. In this connection it should be understood and appreciated that as noted above the gelatin bodies or pellets 20 themselves serve a purpose of marking the biopsy site for a predetermined length of time, that is until they become absorbed by the body.

The drawing figures, particularly FIGS. 1 and 2 show the metal marker 22 disposed substantially in the center of the cylindrical gelatin pellet 20. This is preferred but is not necessary for the present invention. The metal marker 22 can be embodied in or included in the gelatin body 20 virtually anywhere. The gelatin body or pellet 20 however has to have sufficient integrity or firmness to retain the metal marker 22 and air bubbles which are usually deliberately entrapped in the gelatin. As is known, the firmness or bodily integrity of gelatin is measured in units of Bloom. Generally speaking it was found in accordance with the present invention that the higher the Bloom strength of the gelatin used in the marker 20 the better the marker performs. The higher Bloom strength gelatin holds gas bubbles within its matrix better than lower Bloom strength gelatin. Gelatin with a Bloom strength of approximately 150 especially 175 is adequate for the practice of the present invention, but a more preferred range is 200 to 300 Bloom, the most preferred range being between 250 and 300. (For comparison, typical food gelatin is approximately 75 Bloom, and gelatin of 300 Bloom feels like a soft rubber eraser.)

A description how to obtain gelatin or reconstituted collagen bodies suitable for use as markers 20 with various properties, before the permanent radio-opaque metal or like marker 22 of specific form is incorporated therein, is provided below in connection with following examples.

EXAMPLE OF RADIOGRAPICALLY VISIBLE/ PALPABLE MARKER MATERIAL FORMED OF METAL IONS IN COMBINATION WITH A COLLAGENOUS OR GELATINOUS MATRIX

U.S. Pat. No. 4,847,049 (Yamamoto incorporated herein by reference) describes an ion-impregnation or chelation technique whereby an ion may be impregnated or chelated to collagen for the purpose of imparting antimicrobial properties to the collagen preparation. Thus, using this technique, imageable ions such as radiographically visible metal ions, may be bound to a bulky collagenous material to form a marker 10 that may be a) imaged by radiographic means and b) located by palpation of tissue surrounding the biopsy site. For example, a silver ion-renatured collagen composition may be prepared by the following process:

Step 1—Renaturation of Collagen (or Gelatin)

Collagen may be renatured to an insoluble form by processing of denatured collagen that has been obtained from a natural source such as bovine corium (hide), bovine tendon, and porcine skin. Alternatively, pre-processed, insoluble collagen may be purchased in the form of a commercially available hemostatic material such as Collastat™ and Avitene™ nonwoven web. Methods for renaturing collagen are known in the literature, including, for example, those methods described in U.S. Pat. Nos. 4,294,241 and 3,823,212. The specifications of U.S. Pat. Nos. 4,294,241 and 3,823,212 are incorporated herein by reference.

A particularly preferred form of renatured collagen for utilization in accordance with the present invention is one that has been renatured and covalently cross-linked. This collagen may be prepared by utilizing readily available polyfunctional cross linking agents or fixatives, such as dialdehydes, dicarboxylic acids, diamines, and the like. Typically, tropocollagen is dissolved in a buffer of pH 3.0 to 5.0 to provide a solution containing approximately 1 to 2% by weight of the collagen. Then 1% of a dialdehyde cross-linking agent such as glutaraldehyde or formaldehyde is then added. The mixture is then frozen and stored for approximately 24 hours. After thawing and washing to remove unreacted cross linking agent, the renatured cross-linked collagen is then ready for contact with a silver ion-containing solution.

Step 2—Binding of Metal Ions to the Renatured Collagen

The source of silver ion may be a water soluble silver salt, preferably silver nitrate. While the concentration of the silver ion in the solution is not particularly critical, it will be usually convenient to utilize solutions in the concentration range of about 10 to 10 millimolar.

The renatured collagen is preferably contacted with a silver ion-containing solution in the pH range of about 4 to 9. The pH of the silver ion-containing solution can be controlled by the addition of an appropriate titrating agent, such as nitric acid, or potassium hydroxide, as required, to maintain the pH at less than about 9.0 to avoid the degradation of the silver. There is not believed to be any lower limit for the pH, however, normally a pH above 4.0 will be convenient. A particularly preferred range for the pH is from 7.0 to 7.5. The binding capacity of silver by collagen is particularly effective within this preferred pH range, although the amount of binding by silver by the collagen is further controllable by the concentration of the silver ion-containing solution and/or exposure time of the collagen to the silver ion-containing solution. Simultaneous with or subsequent to exposure of the collagen to the silver ion-containing solution, the collagen is then exposed to ultraviolet radiation of energy and duration sufficient to strengthen the binding of the silver ions to the collagen without substantial formation of metallic silver formed as a result of oxidation of various functional groups in the collagen by the silver ion. While the exact limits of the ranges of the conditions which will be sufficient to strengthen the binding of the silver ions without substantial formation of metallic silver are not precisely determinable, it will generally suffice to maintain the pH of the silver-collagen environment at less than 8.0 while exposing the collagen to ultraviolet radiation in the range of about 210 to 310 nm wavelength for about from 5 to 15 minutes. The time of UV exposure for complete reaction is inversely proportional to the light intensity which is preferably in the range of 100 to 1,000 microwatts/cm$^2$. A slight coloration of the collagen due to the exposure to ultraviolet radiation is acceptable, i.e., a turning from white to a light brown to yellow color, indicating a slight oxidation reaction occurring in the collagen, however, the radiation should not be to the extent that dark brown or black areas in the collagen occur due to over-oxidation and/or substantial formation of metallic silver. Normally the exposure will be performed at ambient temperatures, i.e., in the range of about 20 degrees to 25 degrees C., however, there is not believed to be any reason why the exposure could not occur at higher or lower temperatures providing that the temperature is not high enough to cause degradation of the collagen and/or silver ion. There is not believed to be any lower limit to the temperature at which the exposure may take place, provided it is above the freezing point of the ion-containing solution. Ultraviolet radiation may be provided by any conventional ultraviolet radiation source of appropriate wavelength, such as germicidal lamps and mercury/xenon lamps.

Step 3 (Optional)—Addition of Visible Marker Component to the Collagen or Gelatin Matrix If it is desired for the marker to be detectable visually, as well as by imaging and palpation, a quantity of a visible substance having a color dissimilar blood or tissue may be added. For example, carbon particles or a dye (e.g., methylene blue, indigo) may be added to the above-prepared silver ion/collagen preparation to provide a colored silver ion/collagen marker 10 that is imageable (by radiographic means), palpable (by hand) and visible (under white light in the operating room).

The above-described collagen-metal ion marker 10 (with or without visible marker component) is introduced into the cavity created by removal of the biopsy specimen. The quantity of this marker 10 introduced may be sufficient to distend or stretch the biopsy cavity somewhat, thereby creating a more palpable and obvious mass of marker material at the biopsy site.

Renatured gelatin or a cross-linked gelatin preparation such as Gelfoam™ may be impregnated or combined with a metal ion to provide a gelatin-metal ion marker material. The gelatin may be prepared and ion-bound by the same method as set forth hereabove for collagen.

EXAMPLE OF RADIOGRAPHICALLY OR ULTRASONICALLY VISIBLE/PALPABLE MARKER MATERIAL FORMED OF A GAS IN COMBINATION WITH A COLLAGENOUS OR GELATINOUS MATRIX

Step 1—Renaturation of Collagen (or Gelatin)

Collagen or gelatin is renatured, as by the method described in Step 1 of the immediately preceding example and described in the literature, including, for example, those methods described in U.S. Pat. Nos. 4,294,241 and 3,823,212.

Step 2—Dispersing of Air or Other Gas in the Renatured Collagen or Gelatin Matrix Air or another biologically inert gas (e.g., carbon dioxide) is then dispersed throughout the renatured collagen or gelatin matrix by a suitable means such as mixing, mechanical blending, nucleation, bubbling, etc. This results in the formation of many small gas bubbles throughout the collagenous or gelatinous matrix and provides a marker substance that can be introduced into the biopsy cavity through a cannula or tube and is substantially more radio-lucent than the tissue surrounding the biopsy cavity. In this regard, this marker can be imaged by x-ray or ultrasound but will not block or obscure imaging of tissue that lies immediately adjacent the biopsy cavity. Also, because of the bulk of the collagen or gelatin matrix, the marker is readily palpable and locatable by tactile means within the surrounding breast tissue or other tissue.

Step 3 (Optional)—Addition of Visible Marker Component

If it is desired for the marker to be detectable visually, as well as by imaging and palpation, a quantity of a visible substance having a color dissimilar to blood or tissue may be added. For example, carbon particles or a dye (e.g., methylene blue, indigo) may be added to the above-prepared silver ion/collagen preparation to provide a colored silver ion/collagen marker 10 that is imageable (by radiographic means), palpable (by hand) and visible (under white light in the operating room).

In routine use, the above-described collagen/gas or gelatin/gas marker 10 (with or without visible marker component) is introduced into the cavity created by removal of the biopsy specimen. The quantity of this marker 10 introduced may be sufficient to distend or stretch the biopsy cavity somewhat, thereby creating a more palpable and obvious mass of marker material at the biopsy site.

PREFERRED EXAMPLE OF PREPARING CYLINDRICALLY SHAPED GELATIN PELLETS 20 HAVING A COLORANT AND INCLUDING THE PERMANENT MARKER 22

80 grams of dry gelatin obtained from porcine skin is mixed into 1000 ml of hot water (180° F.). Variations in gelatin to water ratio will change the consistency but are nevertheless permissible within the scope of the invention. The 80 grams of gelatin is about the maximum amount which will dissolve in water without modifications to pH. The gelatin is then fully dissolved in the water with slight mixing. In a separate container, 1.6 grams of indigo colorant is mixed into 20 ml of ethyl alcohol. Then the ethanol solution of the colorant is added by mixing to gelatin dissolved in water. Air is then whipped into gelatin mixture to froth the mixture.

The gelatin dissolved in water is then poured into molds (not shown) which have the shape of the desired gelatin body. In the preferred embodiment the mold is shaped to provide the cylindrical pellet shown in the drawing figures. One gamma ($\gamma$) shaped permanent marker 22, made by chemical etching from stainless steel plates, is deposited into the gelatin in each mold. (In alternative embodiments more than one marker 22 may be deposited into each mold.) Due to the viscosity of the gelatin solution the marker 22 does not usually sink to the bottom of the mold. The top of the plate (not shown) holding a plurality of molds is squeegeed to level the mixture.

After cooling to approximately 40° F. or cooler temperature the gelatin sets and provides the gelatin body 20 that incorporates the permanent marker 22 However, in order to dehydrate the marker it is first frozen and thereafter lyophilized in commercial lyophilization apparatus. Gelatin pellets containing the permanent marker 22 but not having a colorant can be prepared in the same manner, but without adding indigo dye or other colorant. Gelatin bodies or markers 20 that do not include or incorporate a permanent marker 22 can also be made in this manner, but without depositing the marker 22 into the gelatin after it has been placed into the mold. The gelatin body 20 prepared in this manner is reabsorbed from the biopsy site by the human body in approximately three weeks, whereas the permanent marker 22 remains indefinitely.

DESCRIPTION OF THE APPLICATOR APPARATUS AND ITS USE IN CONJUNCTION WITH THE BIOPSY MARKER OF THE INVENTION

Figure 5:
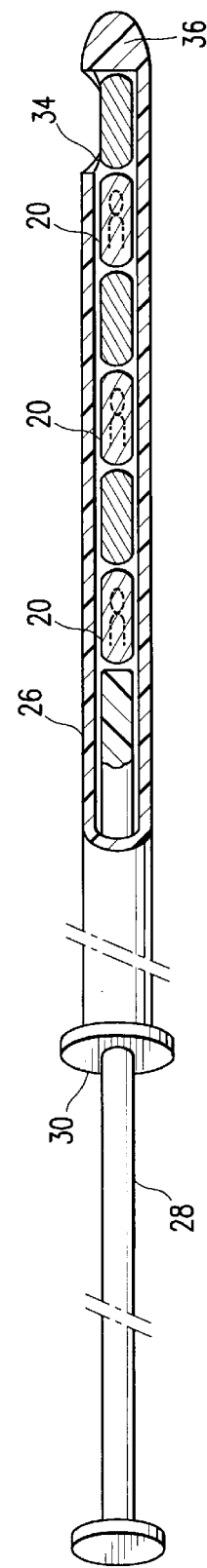
FIG. 5 is a cross-sectional view of the site marker shown in FIG. 4, the cross section taken on lines 5,5 of FIG. 4.
Figure 6:
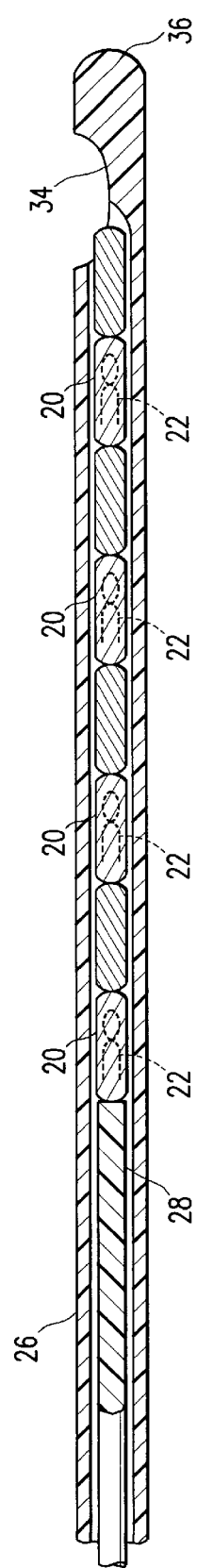
FIG. 6 is an enlarged cross sectional view showing the applicator of FIG. 4 loaded with biopsy site markers in accordance with the present invention.
Figure 7:
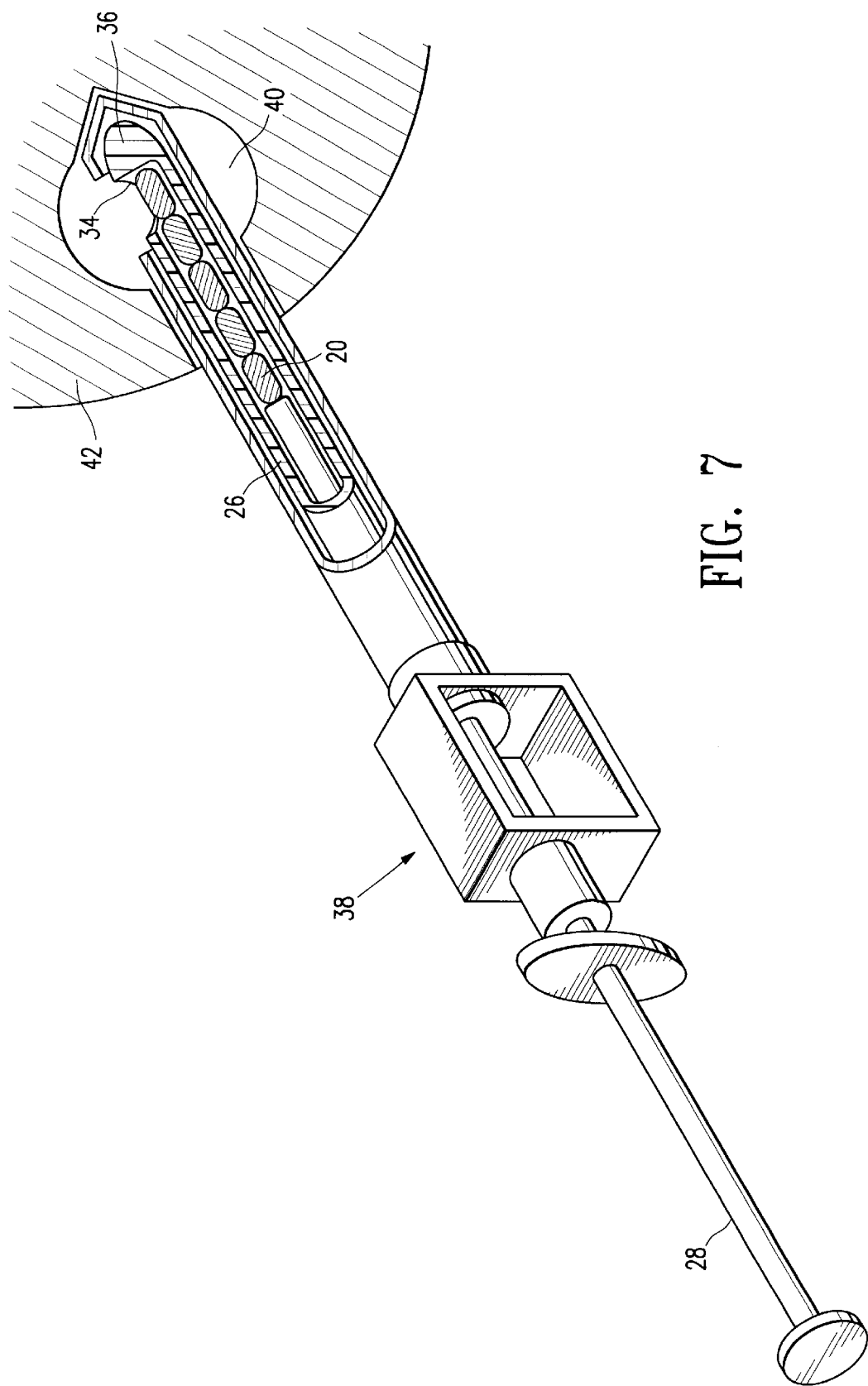
FIG. 7 is a schematic view of a human breast, showing a biopsy cavity of the type obtained by a vacuum assisted large core biopsy sampler, into which a plurality of biopsy markers are deposited in accordance with the present invention.

Referring now to FIGS. 3–7 the applicator device or apparatus 24 with which the biopsy markers of the invention are preferably applied or deposited, is disclosed. In this connection it should be understood that the biopsy markers of the invention can be used without the applicator, and can be deposited in accordance with the various methods and techniques utilized in the state-of-the-art. However, a preferred technique of applying the biopsy markers of the invention is to place or deposit them in a biopsy cavity that is obtained with a vacuum assisted large core biopsy device of the type presently used in the state-of-the-art. Such a device, distributed for example by Johnson and Johnson Endo Surgery is well known in the art, and is schematically shown in FIG. 7.

The applicator 24 of the invention comprises an elongated cylindrical body 26 having an interior cavity and a piston 28 that fits and slides back and forth in the elongated cylindrical body 26. The cylindrical body 26 has an enlarged disk 30 at one end 32. The disk 30 serves to render it convenient for a user (not shown) to operate the applicator 24, as is described below. The cylindrical body 26 that can also be described as an elongated flexible tube has an opening 34 that commences a relatively short distance, that is approximately 0.3" before its other, closed end 36. The opening 34 is configured to form a ramp in the side of the tube 26. The outer diameter of the tube 26 is such that it fits through the vacuum assisted large core biopsy device 38 shown in FIG. 7. In this connection it should of course be understood that the precise dimensions of the tube 26 are coordinated with the dimensions of the piston 28 and with the vacuum assisted large core biopsy device 38. Moreover, the diameter of the gelatin pellets 20 in their dehydrated form are also coordinated with the inner diameter of the cylinder or tube 26. The cylinder or tube 26 and the piston 28 can be made from any appropriate medical grade plastic material, and is preferably made of high density polyethylene. The outer diameter of the presently preferred embodiment of the cylinder or tube 26 is approximately 0.093" and its inner diameter is approximately 0.070".

Figure 4:
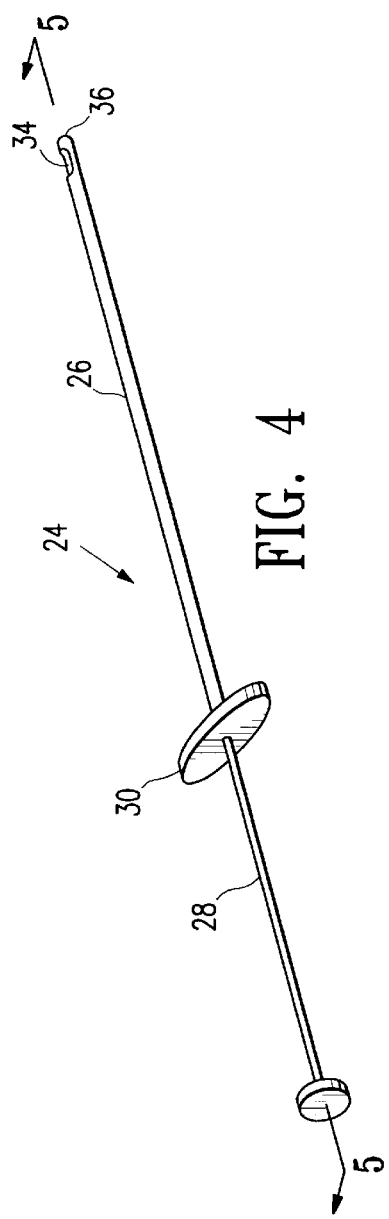
FIG. 4 is a perspective view of the applicator apparatus of FIG. 3, showing the applicator with an extended piston indicating that the applicator is loaded with biopsy site markers.

In the preferred manner of using the biopsy markers of the present invention having the permanent markers 22 incorporated in a gelatin body 20, as well as using biopsy markers that have only the gelatin body 20 without a permanent marker 22, the applicator device 24, more precisely the tube 26 is loaded with a desired number of pellets 20, as is shown in FIGS. 4–6. Any number of pellets 20 within the range of 1 to approximately 30 may be loaded within the tube 26, however presently it appears that approximately 8 pellets 20 are optimal for being loaded into the tube 26 and to be deposited in a biopsy cavity where approximately 1 gram of tissue had been removed. Such a biopsy cavity 40 in a human breast 42 is schematically illustrated in FIG. 7. The pellets 20 which are loaded into the applicator tube 26 may all include the permanent marker 22, but it is presently preferred that only every other pellet 20 loaded into the applicator tube 26 have the permanent marker 22. Such an array of 8 pellets 20, alternating between pellets with and without permanent markers 22 is shown in FIG. 2.

Figure 3:
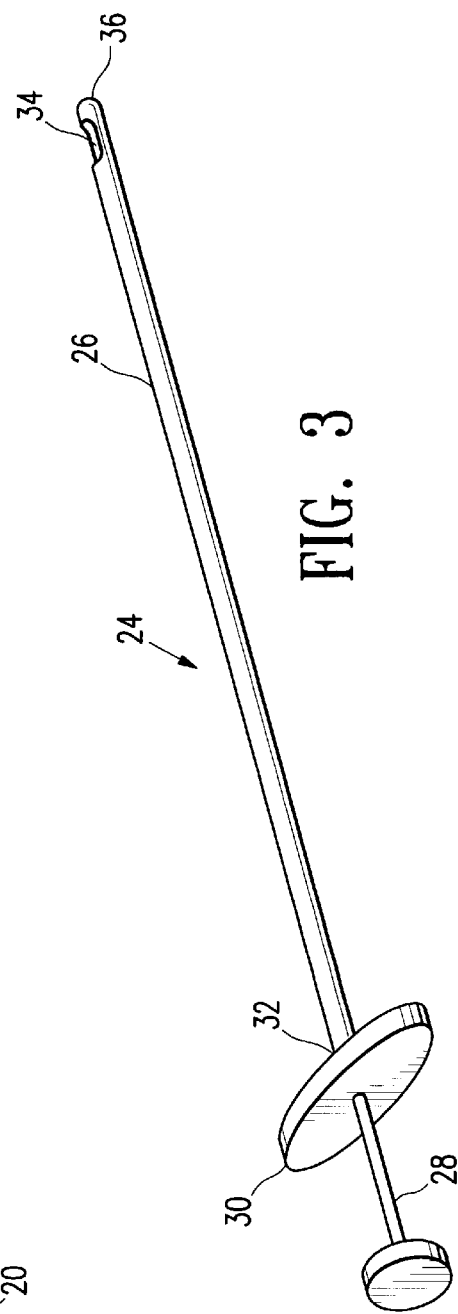
FIG. 3 is a perspective view of an applicator apparatus in accordance with the present invention, for depositing the biopsy site marker at a biopsy site.

When the pellets 20 are in the tube 26 the piston 28 is extended, as is shown in FIGS. 4 and 5. The pellets 20 are expelled one-by-one from the tube 26 through the ramp-shaped opening 34 as the piston 28 is pushed into the cylinder or tube 26. During this process the closed end 36 of the tube 26 is disposed in the cavity 40 formed by biopsy sampling. It is contemplated that the dispersed radio-opaque permanent markers 22 provide a good definition of the entire biopsy cavity 40 for subsequent observation or surgical procedure. FIG. 3 illustrates the applicator device 24 after the pellets 20 have been expelled from the applicator tube 26.

What is claimed is:

1. A marker body which is deliverable to a biopsy site within a patient, comprising
   a preshaped pellet formed of bioabsorbable material having a plurality of gas bubbles dispersed therein which are configured to facilitate ultrasonic observation of the pellet at the biopsy site within the patient, and having an X-ray detectable element of specific predetermined non-biological configuration embedded therein.

2. A marker body in accordance with claim 1 wherein the X-ray detectable element of specific predetermined non-biological configuration comprises metal.

3. A marker body in accordance with claim 2 wherein the X-ray detectable element of specific predetermined non-biological configuration comprises stainless steel.

4. A marker body in accordance with claim 2 wherein the X-ray detectable element of specific predetermined non biological configuration is configured substantially in a shape of a Greek letter gamma (γ).

5. A marker body in accordance with claim 2 wherein the X-ray detectable element consists essentially of an electro-chemically etched stainless steel element.

6. A marker body in accordance with claim 1 wherein the body of bioabsorbable material is configured in the shape of a cylinder.

7. A marker body in accordance with claim 1 wherein the pellet is about 1 to about 3 mm in diameter and is about 5 to about 10 mm long.

8. A marker body in accordance with claim 7 wherein the bioabsorbable material has a Bloom rating in the range between about 150 to about 300 Bloom.

9. A marker body in accordance with claim 1 wherein the bioabsorbable material is gelatin.

10. A marker body in accordance with claim 1 wherein the pellet is approximately 2 mm in diameter and is approximately 8 mm long.

11. An applicator device for a biopsy site marker, the device comprising:
    an elongated cylindrical body that forms a flexible tube and includes a cylindrical cavity having an internal lumen, an open end and a closed end and a ramp within the internal lumen leading to a side opening in the flexible tube in proximity of the closed end; and
    a piston that is moveable back and forth in the cylindrical cavity forming the tube, the tube being configured to be loaded in the internal lumen with a plurality of biopsy site marker bodies according to claim 1 said marker bodies being disposed between the end of the piston and the side opening when the piston is extended outwardly from the cylindrical cavity.

12. An applicator device in accordance with claim 11 wherein the elongated cylindrical body has an internal diameter of approximately 0.070".

13. In combination: an applicator tube having an internal lumen, an open end and a closed end and a ramp shaped opening in proximity of the closed end;
    a flexible rod dimensioned to fit into and be slidable in the internal lumen, and
    a plurality of biopsy site markers comprising a body of dehydrated gelatin, and an X-ray detectable element of specific predetermined non-biological configuration embedded in said body of gelatin, said biopsy site markers being enclosed in the internal lumen, from where they can be pushed out with the flexible rod through the ramp-shaped opening into a biopsy site.

14. The combination in accordance with claim 13 wherein the X-ray detectable element of the biopsy site markers comprises metal.

15. The combination in accordance with claim 13 where the X-ray detectable element of the biopsy site markers comprises stainless steel.

16. The combination in accordance with claim 13 wherein the X-ray detectable element of the biopsy site markers comprises ceramic materials or metal amides.

17. The combination in accordance with claim 13 where the biopsy site markers additionally comprise a plurality of air bubbles embedded in said body of gelatin.

18. The combination in accordance with claim 13 wherein the gelatin of the biopsy site markers has a Bloom rating in the range between approximately 150 to 300 Bloom.

19. The combination in accordance with claim 18 wherein the gelatin of the biopsy site markers has a Bloom rating in the range between approximately 200 to 300 Bloom.

20. The combination in accordance with claim 13 further comprising at least one biopsy site marker that has a body of dehydrated gelatin, and lacks the X-ray detectable element of specific predetermined non-biological configuration embedded in said body of gelatin.

21. The combination in accordance with claim 20 comprising an array of a plurality of said biopsy site markers having said X-ray detectable element of specific predetermined non-biological configuration and a plurality of said biopsy site markers having a body of dehydrated gelatin and lacking the X-ray detectable element of specific predetermined non-biological configuration, said array being enclosed in the internal lumen.

22. The combination in accordance with claim 21 wherein said biopsy site markers having said X-ray detectable element of specific predetermined non-biological configuration and said biopsy site markers having a body of dehydrated gelatin and lacking the X-ray detectable element of specific predetermined non-biological configuration alternate in said array.

23. A marker body which is deliverable to a biopsy site within a patient, comprising:
   a preshaped pellet formed of dehydrated bioabsorbable material having a plurality of gas bubbles dispersed therein which are configured to facilitate ultrasonic observation of the pellet at the biopsy site within the patient, and having an X-ray detectable element of specific predetermined non-biological configuration embedded therein.

* * * * *